United States Patent [19]

Humphrey

[11] 4,189,215
[45] Feb. 19, 1980

[54] METHOD AND APPARATUS FOR THE CORNEAL POSITIONING OF A PATIENT'S EYE

[75] Inventor: William E. Humphrey, Orinda, Calif.

[73] Assignee: Humphrey Instruments Inc., San Leandro, Calif.

[21] Appl. No.: 669,132

[22] Filed: Mar. 22, 1976

[51] Int. Cl.² ............... A61B 3/14; A61B 3/10; A61B 3/00
[52] U.S. Cl. ................................... 351/7; 351/39; 351/6
[58] Field of Search ............ 351/7, 6, 39, 17, 14; 356/172; 350/288; 240/41.35 R

[56] References Cited
U.S. PATENT DOCUMENTS

| | | | |
|---|---|---|---|
| 824,900 | 7/1906 | Bates | 351/17 |
| 3,068,745 | 12/1962 | Peck | 351/14 |
| 3,253,504 | 5/1966 | Vollmer | 240/41.35 |
| 3,857,639 | 12/1974 | Mason | 356/172 |
| 3,879,112 | 4/1975 | Hickey | 350/288 |

OTHER PUBLICATIONS
A. R. Gilliland, Visual Education, vol. Z, Feb. 1921, pp. 21-26, 55.

Primary Examiner—John K. Corbin
Assistant Examiner—Rodney B. Bovernick
Attorney, Agent, or Firm—Townsend and Townsend

[57] ABSTRACT

A method and apparatus are disclosed for accurately positioning a patient's eyes for an eye examination. An eye positioning beam is oriented transversely to the patient's line of sight. A border surface of the beam facing the patient is positioned at the location along the patient's line of sight at which the patient's cornea is to be located during the examination. The patient's head is moved towards the light beam border surface until the border surface and the patient's cornea are tangent. Tangentially is determined by observing an increase in the illumination of the patient's iris. The increased illumination results from a bending and a corresponding reflection of the light rays, which are tangent to the cornea.

31 Claims, 5 Drawing Figures

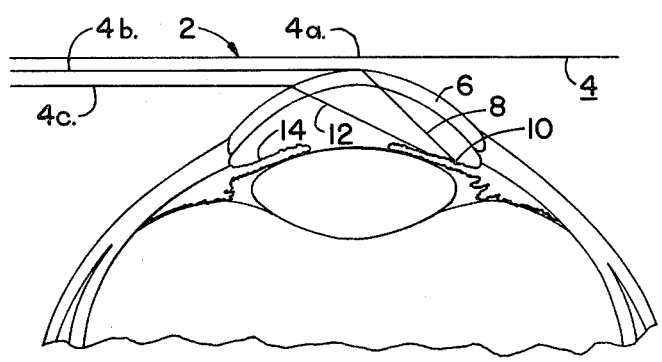
FIG._1.
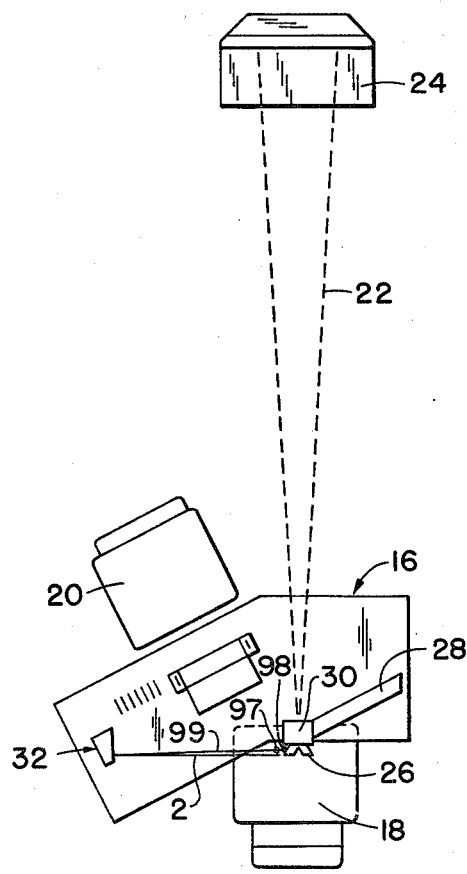
FIG._2.
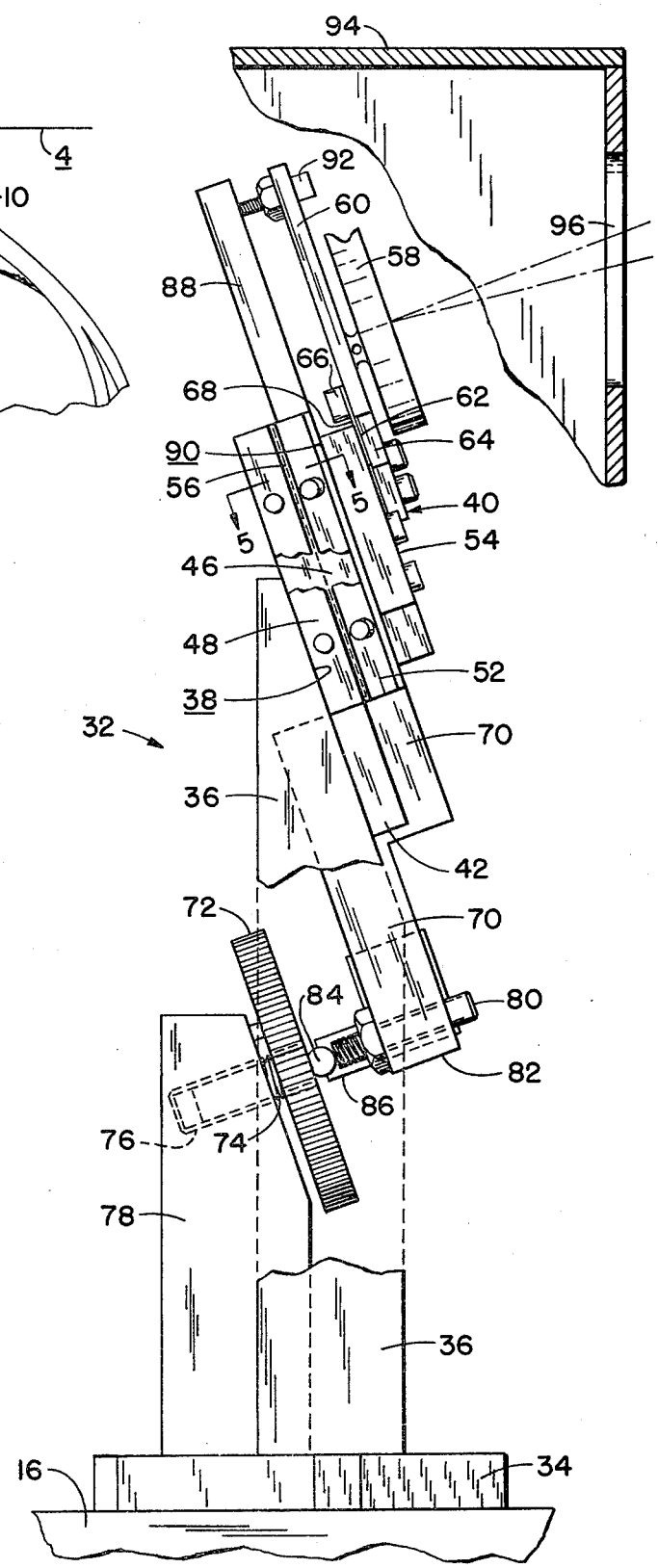
FIG._3.

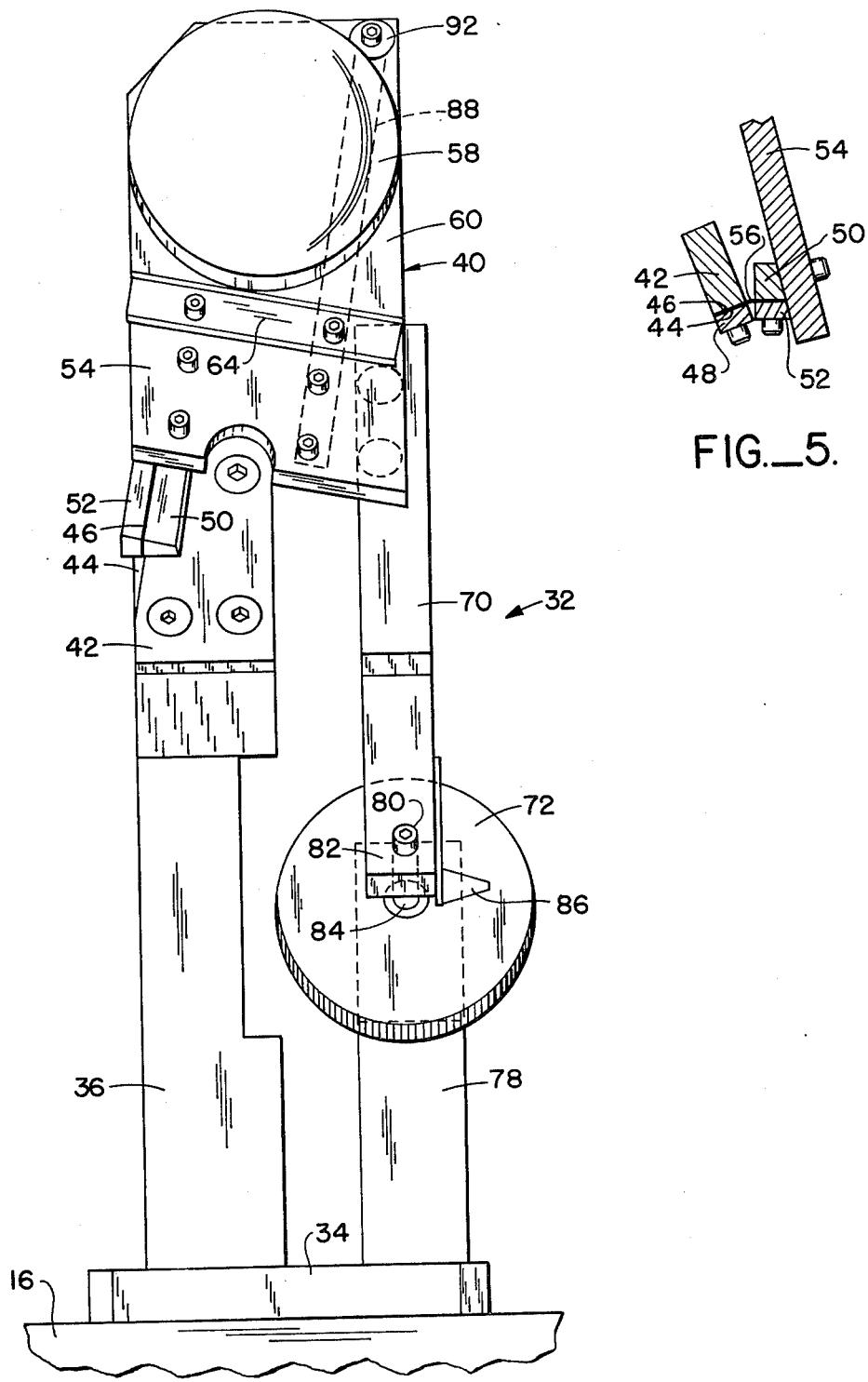
FIG._4.
FIG._5.

METHOD AND APPARATUS FOR THE CORNEAL POSITIONING OF A PATIENT'S EYE

BACKGROUND OF THE INVENTION

During eye examinations it is necessary to precisely position the patient's eye relative to corrective optics employed in the examining process. Historically, a patient's eyes were examined by positioning interchangeable lenses in front of the patient's eye to determine what, if any, sight correction the patient requires. To obtain accurate examination results it is, of course, necessary to precisely position the corrective lenses relative to the patient's eye. This was done with mechanical indicators that were positioned on the side of the patient's head. The examiner had to visually align the indicator with the outer surface of the patient's cornea to place the corrective optics at the desired distance from the patient's eye. This process was relatively inaccurate and most cumbersome because it required the positioning of mechanical measuring devices on the side of the patient's head and further because it required the examiner to observe the patient from his side. The task was both time-consuming and subject to relatively large error rates because the reading was influenced and therefore changed by changes in the position of the examiner relative to the patient's eye and the measuring device. Nevertheless, such measuring devices were widely used in the past because they could be directly attached to the lens holders positioned in front of the patient's face.

U.S. Pat. No. 3,874,774 discloses and claims a new eye testing apparatus which is a radical departure from previously used devices. One of the important features of the testing apparatus disclosed in that patent is the elimination of all lens holders and other measuring devices in front of the patient's eye. Instead, an examination light beam is directed through corrective optics having variable spherical and astigmatic inputs. The corrective optics are placed at a location remote from the patient. Focusing optics in the form of a field mirror are placed between the corrective optics and the patient to focus to the patient a real image of the corrective optics.

When performing an eye examination with this testing apparatus it is of course of the utmost importance that the patient's eyes are at the proper location relative to the focal point of the field mirror to avoid inaccurate or false readings which would render the examination worthless. However, the testing apparatus does not have lens holders in front of the patient's face to which a mechanical measuring device could be attached; consequently it would require additional structure to incorporate prior art eye positioning devices of the type discussed above. More importantly, if such devices were used they would defeat one of the primary objects of the testing apparatus, namely, to provide an unobstructed view of the patient's face, and to remove obstructions from the patient's field of view.

SUMMARY OF THE INVENTION

The present invention enables the accurate positioning of a patient's eyes along his line of sight, e.g., along the examining light beam focused by the field mirror as disclosed in the above referenced U.S. patent, by projecting a positioning light beam transversely to the line of sight (and to the examining light beam) so that the patient's cornea can be brought into tangential relationship with the positioning light beam. When positioning the eye the examiner simply observes the patient's iris. The tangential relationship is established at the moment the illumination of the iris changes, e.g., increases. Thus, an increase in the illumination of the iris signals to the examiner the proper positioning of the eye.

In practice, the present invention contemplates to provide a support for the patient's forehead which is movable in the direction of the patient's line of sight, e.g., in the direction of the examining light beam. The positioning light beam is projected past the patient's eye generally perpendicular to the examining light beam. The border surface of the positioning light beam facing the patient is used as the reference plane for the positioning of the patient's eye. Thus, it is previously set but can be changed for particular examinations within limits as is necessary when examining a patient for wearing spectacles or contact lenses, for example.

To accurately position the patient's eyes, the examiner moves the patient's head support, preferably via remote control, to thereby move the patient's cornea towards a tangential position relative to the border surface of the positioning beam. The examiner observes the patient's iris and terminates the movement of the headrest at the moment an increased illumination of the iris is observed. At that point the patient's cornea is substantially tangent to the border surface of the positioning light beam and, therefore, coincides with the location of the light beam. Knowing the exact location of the patient's eye the examiner can now proceed with the eye examination.

It is apparent that the present invention allows the positioning of the patient's eyes without requiring additional hardware in front or to the side of the patient's face. Thus, the face continues to be in full view of the examiner. Moreover, since the light beam and in particular the border surface facing the patient's eyes can be precisely set the positioning of the patient's eye is equally precise and does not rely on the accuracy with which the examiner positions himself relative to the patient or a mechanical measuring device. Thus, inaccuracies encountered with prior art eye positioning devices are eliminated.

While the present invention assures maximum positioning accuracy, it requires little attention on the part of the examiner and is in particular insensitive to the position, or changes in the position of the examiner relative to the patient or either one of the light beams. All that is required of the examiner is that he observe the patient from the patient's front from a point from which the iris is visible, e.g., in a direction that is angularly inclined relative to the positioning light beam.

Additionally, the present invention provides a continuous check for the examiner on the position of the patient's eyes. If during the examination, the patient should inadvertently move, the examiner can immediately observe a change in the illumination of the iris. Thus, he can take intermittent corrective action by correspondingly moving the patient's headrest in one or the other direction until the patient's cornea is again tangent to the border surface of the light beam. To enhance the ease with which changes in the illumination of the iris are observed, the examination as well as the initial posiitoning of the patient's eyes are preferably conducted in a dark environment.

The present invention also provides the necessary apparatus to carry out the above-described eye positioning method. Broadly speaking, the apparatus comprises a light source which is projected perpendicular to the examination light beam and focused in front of the patient's eyes by a concave mirror. Preferably the light source is an incandescent lamp with an elongate filament, which when focused, generates an elongate slit-like light beam that has a relatively wide border surface facing the patient.

The mirror is pivotable about perpendicular axes so that its position can be adjusted to move the light beam in directions both parallel and perpendicular to the examination light beam. Furthermore, means is provided to move the positioning light beam in a direction parallel to the examination light beam in calibrated increments so that the position of the patient's eyes can be changed by the examiner.

It will be apparent that the present invention first of all provides an eye positioning method and apparatus which is simpler to construct and to manipulate and which is further more accurate than prior art eye positioning devices. Moreover, the present invention greatly facilitates the ease and accuracy with which the eye testing apparatus of the above-referenced U.S. patent can be used. Yet, the simplicity of the present invention renders it relatively inexpensive to construct, maintain and operate.

BRIEF DESCRIPTION OF THE DRAWINGS

FIG. 1 is a fragmentary, cross-sectional illustration of a human eye and schematically shows the method by which the present invention accurately positions a patient's eye;

FIG. 2 is a schematic plan view of an eye examination apparatus fitted with an eye positioning device constructed in accordance with the present invention;

FIG. 3 is an enlarged side elevational view, with parts broken away, and illustrates in greater detail the construction of the eye positioning device of the present invention;

FIG. 4 is a front elevational view of the eye positioning device shown in FIG. 3; and FIG. 5 is a fragmentary, cross-sectional view and is taken on line 5—5 of FIG. 3.

DESCRIPTION OF THE PREFERRED EMBODIMENTS

Referring first to FIG. 1, the present invention employs a positioning light beam 2 which is projected transversely across a patient's line of sight. The positioning light beam includes a border surface 4, preferably relatively wide as measured transverse to the line of sight, and a planar surface as is more fully discussed below, which faces the patient and which is used as the reference plane along the patient's line of sight at which the patient's cornea 6 is to be located during an eye examination.

Initially the light beam and in particular the border surface 4a of the light beam and the cornea 6 are separated. The light beam simply passes the eye without effect. In a dark environment, say in a darkened examination room, the patient's iris remains dark.

If the patient's eye is now moved towards the light beam border surface (or vice versa) the patient's cornea will eventually be tangent to the border surface. That relative position is indicated by line 4b. The cornea deflects the tangent light down (indicated by the inclined line 8) and the deflected rays strike the patient's iris 14 at point 10. If the eye is moved towards the light beam an additional distance, so that border surface 4c intercepts the cap of the patient's cornea, additional light rays are bent down (schematically illustrated by line 12) and they too contact the iris.

The downwardly bent light rays illuminate the patient's iris 14 and cause a corresponding reflection which can be observed by the examiner. The increase in the illumination of the iris is more readily observed when the remainder of the eye is non-illuminated, say in a dark environment.

It is apparent that the suddenly increased illumination of the iris informs the examiner that the patient's cornea is tangent to the border surface of the positioning light beam 2 when the change in the illumination occurs. At that moment he, therefore, arrests the further movement of the patient's head and eye. By moving the patient's head momentarily in the opposite direction he can readily find the virtually exact tangent point of the cornea and the light beam bordering surface. It will also be apparent that the determination of the desired positioning of the patient's eye is not dependent upon the relative positioning of the examiner. The examiner only notes the change in illumination and not relative positions of the patient's eye, the positioning light beam or a measuring object or device.

The positioning apparatus of the present invention will now be described in greater detail as specifically incorporated in an eye testing apparatus constructed in accordance with the above discussed U.S. patent. Referring to FIGS. 2-5, such a testing apparatus broadly comprises a console 16 which has a patient station, preferably defined by a patient chair 18 and an examiner station 20 disposed at the side of the console opposite the patient chair. The console houses a light source and corrective optics (not shown) and projects an examination light beam 22 via a field mirror 24 to the patient station. Details of the construction of the corrective optics, the field mirror, etc. are set forth in the referenced U.S. patent.

The console includes a headrest 26 against which the patient's forehead is placed during an eye examination. The headrest is carried by a cantilevered arm 28 and connected to means 30 for moving the headrest generally parallel to examination beam 22 towards and away from the field mirror.

A projector 32 for generating the eye positioning beam 2 is mounted to the console and projects the beam transversely, e.g. perpendicular to examination light beam 22 past patient chair 18. The light beam is positioned so that its border surface (illustrated in FIG. 1 only) coincides with a predetermined reference point along the examination beam at which the patient's eye is to be positioned during the subsequent eye examination.

Referring now specifically to FIGS. 3-5, positioning beam projector 32 includes a base plate 34 mounted, e.g., bolted to the console 16. A main post 36 projects upwardly from the plate and terminates in a downwardly slanted mounting surface 38. A mirror assembly 40 is bolted to the slanted surface.

The mirror assembly is defined by a first, flat adaptor plate 42 bolted to the slanted mounting surface of the main post and including an angularly offset hinge mounting surface 44. One half of a first, generally vertically oriented, elongate leaf spring 46 is firmly bolted to hinge mounting surface 44 with a clamping bar 48. The other half of the leaf spring protruding past the clamping bar is firmly bolted to an elongate hinge bar 50 with another clamping bar 52. Hinge bar 50 in turn is securely bolted to a generally horizontally extending pivot plate 54.

It will be observed that pivot plate 54 can swing or pivot about an upright, generally vertical axis defined by the unclamped portion 56 of the leaf spring between clamping bars 48 and 52. Thus, the unclamped spring portion forms a hinge about which pivot plate 54 can be pivoted.

A focusing reflector, e.g., a concave mirror 58 is mounted to a mirror base plate 60 which in turn is hingedly connected to the upper edge of pivot plate 54 with a second, elongate, generally horizontally oriented leaf spring 62. Clamping bars 64 and 66 securely bolt the second leaf spring to the pivot plate and the mirror base plate 60 in the above described manner so that an unclamped spring portion 68 remains which forms a hinge for the mirror and the mirror base plate.

Accordingly, the mirror base plate and the mirror can be pivoted relative to pivot plate 54 about a generally horizontally oriented axis defined by unclamped spring portion 68. Also, the mirror and the mirror plate, together with the pivot plate can be pivoted about a generally vertical axis defined by unclamped spring portion 56 of first leaf spring 46 as above defined. Consequently, the mirror orientation can be pivotally changed and adjusted along perpendicular axes. By employing flexible leaf springs as the pivot members, play, which is normally encountered with conventional mechanical hinges, is eliminated.

A pivot arm 70 is mounted to the side of pivot plate 54 opposite from first leaf spring 46, extends downwardly from the pivot plate and terminates at a distance above base plate 34. An adjustment wheel 72 is secured to a threaded shaft 74 which is threaded into a slanted hole 76 in a wheel base 78 mounted to base plate 34. The threaded shaft is positioned so that it is opposite a lower end 82 of pivot arm 70. An adjustment bolt 80 is threaded into the lower pivot arm and has a free end facing the adjustment wheel. A spacer ball 84 is loosely retained in a depression in the adjustment wheel and spaces the free end of adjustment bolt 80 from the wheel. The threaded bolt 74, adjustment wheel 72, adjustment bolt 80 and spacer ball 84 are dimensioned so that they exert a tension on first leaf spring 46. This tension retains the spacer ball in place, and eliminates any play in the pivot connection which, if present, would adversely affect the accuracy of the projector.

By turning the adjustment wheel 72 in one or the other direction, pivot arm 70 is forced in one or the other direction (as seen in FIG. 3) which results in a corresponding pivotal movement of pivot plate 54 and, therewith, of mirror 58 about the pivot axis defined by the unclamped portion 56 of leaf spring 46. A pointer 86 can be mounted to the lower end 82 of the pivot arm and the adjustment wheel can be fitted with suitable graduations to indicate relative positions of the wheel and, thereby of the mirror.

An elongate adjustment bar 88 is bolted to an underside 90 of pivot plate 54 and extends upwardly to about the uppermost end of mirror base plate 60. The adjustment bar is spaced from the underside of the mirror base plate and a set screw 92 is threaded through the mirror base plate. A lower end of the set screw engages the free end of the adjustment bar and maintains the spacing between the adjustment bar and the mirror base plate. By turning the set screw in one or the other direction the base plate and therewith mirror 58 can be pivoted about the generally horizontal pivot axis defined by the unclamped portion 68 of horizontal leaf spring 62.

Projector 32 is bolted to the surface of console 16 at a point thereon so that the position of mirror 58 roughly lies in a plane that is tangent to the patient's cornea when the patient's head is supported by headrest 26. A housing 94 covers the operative components of the projector and prevents persons or objects from accidentally striking any portion of the projector and thereby disturbing its setting. The housing includes a window 96 through which light projected by mirror 58 can pass.

A light source 98 is mounted to the headrest structure 26 at about the same distance from the mirror 58 as the patient's eye. The light 99 from source 98 is directed to mirror 58 through housing aperture 96 and is reflected by the mirror towards the patient's eye.

It is preferred that the light source is an incandescent lamp with an elongate positioning filament that is focused by mirror 58 in the vicinity of the patient's eyes. Thus, the light beam 2 has a relatively wide border surface 4 facing the patient. Such a wide border surface facilitates the use of the beam for the positioning of the patient's eyes because it can accommodate differences in the vertical positioning of the eyes of different patients without requiring a readjustment of the mirror.

A cylinder lens 97 may be placed along the line filament lamp to extend the apparent length of the filament while maintaining its narrow width. Thus, the cylinder lens in effect acts as "magnifier" along the length of the filament.

The installation and operation of projector 32 should now be apparent. To briefly summarize it, after the projector has been mounted to the console, it is set by adjusting mirror 58 so that it reflects positioning light beam 2 in the desired direction. That is, set screw 92 is turned to pivot the mirror about the horizontal pivot axis until border surface 4 of the light beam is at the desired elevation relative to headrest 26. Additionally, adjustment wheel 72 is turned in one or the other direction until the border surface of the positioning light beam is at the exact location along examination light beam 22 at which the patient's cornea is to be located during an eye examination. Suitable positioning jigs and devices which do not form part of this invention are employed in aligning the projector.

After the projector has been properly aligned an eye examination can be performed. The patient seats himself on patient chair 18 and supports his forehead on headrest 26. With the examination room darkened the examiner energizes light source 98 to project positioning beam 2 past the patient's eyes. If the light beam strikes the patient's eyes or face the examiner actuates headrest moving means 30 until the patient's face and eyes are spaced from the positioning light beam.

Thereafter the examiner operates the headrest moving means in the opposite direction to move the patient's head and, therewith, his eyes towards the border surface 4 of the positioning beam 2. At the instant the border surface is tangent to the patient's cornea the patient's iris "lights up". The headrest moving means is de-energized and the examiner knows that the patient's eye is at the proper position for an eye examination. In the event the headrest moving means was permitted to over-travel, so that the patient's eye protrudes into the positioning light beam, the examiner can move the headrest back and forth until the tangent position of the cornea relative to the border surface of the light beam is attained.

In practice a patient is examined for fitting either spectacles or contact lenses. Since the relative position of spectacle lenses and contact lenses is offset by a distance of between 10 to 15 millimeters, the examination for one or the other type of lenses requires a corresponding adjustment of the positioning light beam 2 because the effective location of the corrective optics of the testing apparatus is fixed. Accordingly, the examiner turns adjustment wheel 72 in one or the other direction to pivot the mirror about its upright pivot axis (defined by the unclamped spring portion 56) to thereby move the border surface 4 of the positioning beam over the desired distance in one or the other direction. To facilitate this adjustment the adjustment wheel 72 is preferably provided with suitable calibrations which can be read off with the help of pointer 86.

As mentioned above, during the actual examination process the examiner has free vision of the patient's eyes and can continuously observe the illumination of his iris by the positioning beam. If that illumination changes, say because the patient inadvertently moved his head, the examiner can reposition the patient's eyes by again actuating the headrest moving means 30 until the cornea is tangent to the positioning beam border surface 4.

Although the embodiment of the invention described herein is presently preferred, it is apparent that the advantages of the invention can be equally obtained by changing specific structural details of the disclosed apparatus. For example, instead of positioning the light source 98 in the headset 26, it can be incorporated within housing 94. Adjustments in the relative position of the examination beam 2 can also be made by moving the light source instead of the mirror and by incorporating a focusing lens between the mirror and the examination station, a flat mirror can be employed while still focusing the light source at the patient's eye for the advantages described above. Such changes are, of course, within the scope of this invention.

I claim:

1. A method for determining the position of a patient's eye during an eye examination comprising the steps of: generating a light beam which is substantially perpendicular to and traverses the patient's line of sight at the desired position of the patient's eye along a line of sight; moving the light beam and the patient's head relative to each other in the direction of the line of sight; and observing when the light beam is substantially tangent to the patient's cornea, whereby the iris of the patient's eye becomes illuminated with increased illumination when the position of the patient's cornea along his line of sight coincides with that of the light beam.

2. A method according to claim 1 wherein the step of observing comprises the step of observing the patient's eye in a direction which is angularly inclined with respect to beam.

3. A method according to claim 1 wherein the step of observing comprises the step of viewing the patient's eye from the patient's front, and terminating the moving step in response to a change in the illumination of the patient's iris.

4. A method for determining the relative position of a patient's eye along the patient's line of sight comprising the steps of generating a light beam oriented transversely to the line of sight, moving the patient and the light beam relative to each other in the direction of the line of sight, observing the patient's iris, and terminating the moving step in response to the observation of a change in the illumination of the iris, whereby the patient's cornea is substantially tangential to the light beam when the change is first observed and the relative position of the patient's cornea and of the light beam along the line of sight coincide.

5. A method according to claim 4 wherein the step of observing the patient's iris is performed by observing the iris in a direction which is angularly inclined relative to the light beam.

6. A method according to claim 4 wherein the step of moving the patient and the light beam relative to each other comprises the steps of supporting the patient's forehead with a headrest, and moving the headrest parallel to the line of sight to thereby cause the relative movement between the patient's eye and the light beam.

7. A method according to claim 4 wherein the step of generating the light beam includes the step of generating a slit-like light beam having a thickness in the direction of the line of sight and a transverse width which is greater than its thickness.

8. A method according to claim 7 including the step of positioning the light beam perpendicular to the line of sight.

9. In a method of examining a patient's eye by supporting the patient's head and directing a first light beam in the direction of the patient's line of sight to the patient's eye, and locating the patient's eye along the first light beam, determining with the first light beam any optical correction required for the patient's eye, the improvement to the step of locating the patient's eye comprising the steps of: providing a support for the patient's head which is movable in the direction of the first light beam; generating a second light beam which extends past the patient's eye and transversely intercepts the first light beam, the second beam defining a light beam border surface facing the patient's eye; positioning the second beam with the border surface intercepting the first light beam at a desired location thereon; moving the support to thereby move the patient's head and the eye in the direction of the first light beam to move the second light beam and the patient's cornea towards relative tangential positions; observing the patient's iris in a direction which is non-parallel with respect to the second light beam; and terminating the moving step at the instant of and in response to a change in the illumination of the iris; whereby the cornea of the patient's eye is positioned tangentially to the border surface of the second light beam and the location of the cornea along the first light beam coincides with that of the border surface.

10. A method according to claim 9 wherein the step of generating the second light beam comprises the step of generating the second light beam with a substantially planar border surface, and positioning the planar surface perpendicular to the first light beam.

11. A method according to claim 9 including the step of changing the direction from which the patient's eye is observed during the observing step.

12. A method according to claim 9 including the step of intermittently moving the head support during the step of determining the optical correction required for the patient's eye in response to changes in the observed illumination of the patient's iris to thereby maintain the patient's cornea at the desired location on the first light beam.

13. Apparatus for positioning a patient's eye at a predetermined location along the patient's line of sight comprising: means for generating a light beam having a light beam border surface facing the patient and intercepting the line of sight at the point at which the patient's cornea is to be located; and means for moving the patient's eye and the light beam relative to each other in the direction of the line of sight to position the patient's cornea tangentially with respect to the light beam border surface; whereby an observer can determine the positioning of the cornea at the desired location by observing a change in the illumination of the patient's iris.

14. Apparatus according to claim 13 wherein the means for generating the light beam includes a light source and means for reflecting a light beam from the light source transversely to the line of sight.

15. Apparatus according to claim 14 wherein the reflecting means comprises a concave mirror.

16. Apparatus according to claim 15 wherein the mirror has a focal length substantially equal to the distance between the mirror and the patient's eye.

17. Apparatus according to claim 16 wherein the light source comprises a filament lamp having an elongated filament substantially perpendicular to the line of sight, and including a cylinder lens disposed between the light source and the mirror for extending the apparent length of the filament focused by the mirror.

18. Apparatus according to claim 14 including means for generating a light beam in which said border surface is a planar surface disposed substantially perpendicular to the line of sight.

19. Apparatus according to claim 14 including means for pivoting the reflecting means about a first axis for moving the light beam border surface along the line of sight.

20. Apparatus according to claim 19 including means for pivoting the reflecting means about a second axis substantially perpendicular to the first axis for moving the border surface in a direction substantially perpendicular to the line of sight.

21. An eye testing apparatus comprising a console having a patient station and an examiner's station; headrest means for supporting a patient's forehead in a generally upright position; means for directing a focused eye examination light beam to at least one of the patient's eyes; and means for accurately positioning the patient's eyes along the examination light beam including means projecting an eye positioning beam transversely to the examination beam, the eye positioning beam defining the location on the eye examination beam at which the patient's eyes are to be located during the eye examination; and means for moving the headrest transversely to the positioning beam to bring the patient's eyes into registration with the positioning beam.

22. Apparatus according to claim 21 wherein the projecting means includes means for adjusting the location of the positioning means in a direction transverse to the examination beam.

23. Apparatus according to claim 21 including means for adjusting the positioning beam in a direction generally parallel to the examination beam.

24. Apparatus according to claim 21 wherein the projector includes a light source, and means for projecting light from the source to generate the positioning light beam.

25. Apparatus according to claim 24 wherein the projecting means comprises a focusing mirror having a focal point in the vicinity of the patient's eyes when the patient's head is supported by the headrest means.

26. Apparatus according to claim 21 wherein the examiner station is located generally opposite the patient station and between the examination light beam and the positioning light beam projecting means.

27. Apparatus according to claim 21 wherein the positioning light beam projecting means includes a light source and means for projecting light from the source as the positioning light beam past the patient's eyes.

28. Apparatus according to claim 27 wherein the projecting means comprises a mirror, and including first and second pivot means permitting pivotal movement of the mirror about generally upright and horizontal axes, respectively; and means for causing pivotal movements of the mirror about said axes.

29. Apparatus according to claim 28 wherein the means for causing pivotal movements of the mirror about the upright axis comprises a calibrated adjustment wheel mounted to the projector and connected with the mirror.

30. Apparatus according to claim 28 wherein the first and second pivot means are defined by elongate leaf springs having fixed lateral sides and a free intermediate portion, the free portion defining said pivot axes.

31. An eye testing apparatus comprising:
a console having a patient station and an examiner's station generally opposite the patient station;
headrest means for supporting a patient's forehead in a generally upright position;
means for directing an eye examination light beam to at least one of the patient's eyes; and
means for projecting a slit-shaped eye positioning beam transversely to the examination beam, the eye positioning beam intercepting the examination beam and defining the location on the eye examination beam at which the patient's eyes are to be located during an eye examination;
the examiner's station being positioned between the eye examination beam and the eye positioning beam;
means for moving the headrest transversely to the positioning beam to bring the patient's eyes into registration with the positioning beam;
the projecting means including
(i) means for focusing the positioning beam in the vicinity of the patient's eyes and for orienting the beam so that its relatively wider border surface faces the patient, the border surface defining the location of the patient's cornea along the examination beam;
(ii) a support structure for the focusing means mounted to the console;
(iii) first and second, generally perpendicular leaf springs and spaced-apart means firmly clamping lateral side portions of each leaf spring, the clamping means being operatively connected with the support structure and the focusing means; whereby each leaf spring includes an unclamped center portion, the center portions of the springs being perpendicular with respect to each other and defining perpendicular pivot axes about which the focusing means can be pivoted relative to the support structure;
(iv) means for pretensioning the leaf springs to thereby connect the focusing means with the support structure in a vibration and motionless manner; and
(v) means for causing pivotal movement of the focusing means about the perpendicular center portions of the springs while maintaining the springs pretensioned for adjusting the direction in which the focusing means projects the positioning beam.

* * * * *